US009110446B2

(12) United States Patent
Kasper et al.

(10) Patent No.: US 9,110,446 B2
(45) Date of Patent: Aug. 18, 2015

(54) DYE-BASED TIME-INDICATING LABEL

(71) Applicant: Brady Worldwide, Inc., Milwaukee, WI (US)

(72) Inventors: Matthew M. Kasper, Oak Creek, WI (US); Adam D. Scheuer, Fox Point, WI (US); Michael D. Savagian, Bryant, WI (US)

(73) Assignee: Brady Worldwide, Inc., Milwaukee, WI (US)

( * ) Notice: Subject to any disclaimer, the term of this patent is extended or adjusted under 35 U.S.C. 154(b) by 436 days.

(21) Appl. No.: 13/712,549

(22) Filed: Dec. 12, 2012

(65) Prior Publication Data

US 2014/0158039 A1    Jun. 12, 2014

(51) Int. Cl.
| | | |
|---|---|---|
| *G01N 21/75* | (2006.01) | |
| *G04F 13/00* | (2006.01) | |
| *G04F 1/00* | (2006.01) | |
| *B41M 5/395* | (2006.01) | |
| *G09F 3/04* | (2006.01) | |
| *H01B 7/36* | (2006.01) | |

(Continued)

(52) U.S. Cl.
CPC *G04F 13/00* (2013.01); *G04F 1/00* (2013.01); *G09F 3/0291* (2013.01); *B41M 5/395* (2013.01); *B41M 5/42* (2013.01); *B41M 5/52* (2013.01); *C09D 11/50* (2013.01); *F16L 1/11* (2013.01); *G01N 21/78* (2013.01); *G01N 31/22* (2013.01); *G01N 31/223* (2013.01); *G01N 33/521* (2013.01); *G01N 33/545* (2013.01); *G01N 33/54386* (2013.01); *G04F 1/06* (2013.01); *G04F 13/06* (2013.01); *G09F 3/0295* (2013.01); *G09F 3/04* (2013.01); *G09F 3/06* (2013.01); *G09F 7/18* (2013.01); *H01B 7/368* (2013.01); *H01B 13/344* (2013.01)

(58) Field of Classification Search
CPC . G01N 21/78; G01N 33/54386; G01N 31/22; G01N 31/223; G01N 33/521; G01N 33/545; G04F 1/00; G04F 1/06; G04F 13/06; G04F 13/00; B41M 5/392; B41M 5/395; B41M 5/42; B41M 5/52; F16L 1/11; G09F 7/18; G09F 3/04; G09F 3/06; G09F 3/0295; H01B 13/344; H01B 7/368; C09D 11/50
See application file for complete search history.

(56) References Cited

U.S. PATENT DOCUMENTS

| | | |
|---|---|---|
| 5,602,804 A | 2/1997 | Haas |
| 5,633,835 A | 5/1997 | Haas et al. |

(Continued)

*Primary Examiner* — Dennis M White
(74) *Attorney, Agent, or Firm* — Whyte Hirschboeck Dudek S.C.

(57) ABSTRACT

A multilayer time indicator comprises:
A. A topsheet,
B. An activating layer,
C. A timing layer,
D. A dye layer, and
E. A substrate.
In one embodiment the topsheet and activating layer comprise a first or activation section of the indicator while the timing layer, dye layer and substrate comprise a second or base section of the indicator. In one embodiment the activating layer of the first section and the timing layer of the second section are each protected with a release sheet. In one embodiment, the first and second sections of the indicator comprise a kit which can be converted into an active time indicator by removal of the release sheets and joining of the activating layer to the timing layer. In one embodiment the first and second section are joined to one another by a common release sheet or liner which maintains the indicator in an inactive state until the release sheet is removed and the activating layer is joined to the timing layer.

16 Claims, 7 Drawing Sheets

(51) Int. Cl.
| | | |
|---|---|---|
| G01N 33/543 | (2006.01) | |
| G01N 21/78 | (2006.01) | |
| G09F 3/06 | (2006.01) | |
| C09D 11/50 | (2014.01) | |
| H01B 13/34 | (2006.01) | |
| G09F 7/18 | (2006.01) | |
| B41M 5/42 | (2006.01) | |
| G04F 1/06 | (2006.01) | |
| G04F 13/06 | (2006.01) | |
| G01N 31/22 | (2006.01) | |
| F16L 1/11 | (2006.01) | |
| G09F 3/00 | (2006.01) | |
| G01N 33/545 | (2006.01) | |
| G01N 33/52 | (2006.01) | |
| B41M 5/52 | (2006.01) | |

(56) References Cited

U.S. PATENT DOCUMENTS

| | | |
|---|---|---|
| 5,822,280 A | 10/1998 | Haas |
| 6,452,873 B1 | 9/2002 | Holt et al. |
| 2004/0013839 A1 | 1/2004 | Ko et al. |
| 2005/0185520 A1 | 8/2005 | Haas et al. |

DYE-BASED TIME-INDICATING LABEL

BACKGROUND OF THE INVENTION

1. Field of the Invention

This invention relates to time-indicating labels. In one aspect the invention relates to multilayer, dye-based labels while in another aspect, the invention relates to labels comprising a top sheet, activating layer, timing layer, dye and a substrate.

2. Description of the Related Art

Numerous devices are known which provide, after activation, a visual indication of the passage of a predetermined period of time. Such time indicators are useful, for example, as a security badge, as an indicator of the length of time a perishable item has been on the wholesaler's or retailer's shelf, and for numerous other uses.

One problem that generally exists with such a time indicators is that they gradually change color over a period of time and it is difficult to ascertain the actual completion of the time interval, i.e., it is a "grey" time interval. For a time indicator to be useful, its appearance should not change for at least 70% of its intended life. Such a time indicator would remain until near the end of the time interval for which it was created, and then the color (or image) rapidly would appear. In essence, what is desirable is a time switch meaning a rapid color change to clearly show that the time interval has ended.

U.S. Pat. No. 5,822,280 and the references cited within it describe various attempts at devising time indicators that provide this step function. While most perform in an acceptable manner, all are subject to improvement.

SUMMARY OF THE INVENTION

In one embodiment the invention is a multilayer time indicator comprising:

A. A topsheet,
B. An activating layer,
C. A timing layer,
D. A dye layer, and
E. A substrate.

In one embodiment the topsheet and activating layer comprise a first or activation section of the indicator while the timing layer, dye layer and substrate comprise a second or base section of the indicator. In one embodiment the activating layer of the first section and the timing layer of the second section are each protected with a release sheet. In one embodiment, the first and second sections of the indicator comprise a kit which can be converted into an active time indicator by removal of the release sheets and joining of the activating layer to the timing layer. In one embodiment the first and second section are joined to one another by a common release sheet or liner which maintains the indicator in an inactive state until the release sheet is removed and the activating layer is joined to the timing layer.

In one embodiment the invention is an activated, multilayer time indicator comprising:

A. A translucent or transparent topsheet comprising a polymeric film having first and second facial surfaces, B. An activating layer having first and second facial surfaces, the first facial surface of the activating layer in contact with the second facial surface of the topsheet, the activating layer comprising a plasticizer and a polymer resin in which the plasticizer comprises 20-80 weight percent (wt %) of the activating layer, C. A timing layer having first and second facial surfaces, the first facial surface of the timing layer in direct contact with the second facial surface of the activating layer, the timing layer comprising a polymer resin and an opaque pigment in which the polymer resin has a weight average molecular weight of 5,000 to 1,000,000 grams per mole and a Tg of greater than 25° C., the polymer resin comprising 15-85 wt % of the timing layer sufficient to achieve an opacity of at least 90% per ASTM D2805.

D. A dye layer having first and second facial surfaces, the first facial surface of the dye layer in direct contact with the second facial surface of the timing layer, the dye layer comprising a polymer resin and a dye in which the polymer resin has a weight average molecular weight of 5,000 to 1,000,000 grams per mole and a Tg of greater than 25° C. and the dye soluble in each of (i) an organic solvent, (ii) the polymer resin of both the dye and timing layers, and (iii) the plasticizer of the activating layer, the dye present in the dye layer at a concentration of 1-30 parts solids based on the total solids of the dye layer, and E. A substrate having first and second facial surfaces, the first facial surface of the substrate in direct contact with the second facial surface of the dye layer, the substrate inert to the plasticizer of the activating layer.

In one embodiment the dye of dye layer D is soluble in the solvent. In one embodiment dye particles are dispersed in a solvent with an insoluble resin binder. In one embodiment the activated, multilayer time indicator further comprises a pressure sensitive adhesive (PSA) layer for mounting the label to a substrate. In one embodiment the activated, multilayer time indicator further comprises a release liner to protect the PSA layer.

In one embodiment the invention is an inactive multilayer time indicator comprising:

A. A translucent or transparent topsheet comprising a polymeric film having first and second facial surfaces, B. An activating layer having first and second facial surfaces, the first facial surface of the activating layer in contact with the second facial surface of the topsheet, the activating layer comprising a plasticizer and a polymer resin in which the plasticizer comprises 20-80 wt % of the activating layer, C. A release sheet having first and second facial surfaces, the first facial surface of the release sheet in direct contact with the second facial surface of the activating layer, the release sheet a block to the migration of the plasticizer out of the activating layer, D. A timing layer having first and second facial surfaces, the first facial surface of the timing layer in direct contact with the second facial surface of the release sheet, the timing layer comprising a polymer resin and an opaque pigment in which the polymer resin has a weight average molecular weight of 5,000 to 1,000,000 grams per mole and a Tg of greater than 25° C., the polymer resin comprising 15-85 wt % of the timing layer, sufficient to achieve an opacity of at least 90% per ASTM D2805, E. A dye layer having first and second facial surfaces, the first facial surface of the dye layer in direct contact with the second facial surface of the timing layer, the dye layer comprising a polymer resin and a dye in which the polymer resin has a weight average molecular weight of 5,000 to 1,000,000 grams per mole and a Tg of greater than 25° C. and the dye soluble in each of (i) an organic solvent, (ii) the polymer resin of both the dye and timing layers, and (iii) the plasticizer of the activating layer, the dye present in the dye layer at a concentration of 1-30 parts solids based on the total solids of the dye layer, and F. A substrate having first and second facial surfaces, the first facial surface of the substrate in direct contact with the second facial surface of the dye layer, the substrate inert to the plasticizer of the activating layer.

In one embodiment the dye of dye layer E is soluble in the solvent. In one embodiment dye particles are dispersed in a solvent with an insoluble resin binder. In one embodiment the activated, multilayer time indicator further comprises a pressure sensitive adhesive (PSA) layer for mounting the label to a substrate. In one embodiment the activated, multilayer time indicator further comprises a release liner to protect the PSA layer.

In one embodiment the invention is a two-section, inactivate, multilayer time indicator kit comprising:

A. A first section comprising:
1. A translucent or transparent topsheet comprising a polymeric film having first and second facial surfaces,
2. An activating layer having first and second facial surfaces, the first facial surface of the activating layer in contact with the second facial surface of the topsheet, the activating layer comprising a plasticizer and a polymer resin in which the plasticizer comprises 20-80 wt % of the activating layer, and
3. A release sheet having first and second facial surfaces, the first facial surface of the release sheet in direct contact with the second facial surface of the activating layer, the release sheet a block to the migration of the plasticizer out of the activating layer, and B. A second section, separate and apart from the first section, comprising:
4. An optional release sheet having first and second facial surfaces,
5. A timing layer having first and second facial surfaces, the first facial surface of the timing layer in direct contact with the second facial surface of the release sheet, the timing layer comprising a polymer resin and an opaque pigment in which the polymer resin has a weight average molecular weight of 5,000 to 1,000,000 grams per mole and a Tg of greater than 25° C., the polymer resin comprising 15-85 wt % of the timing layer,
6. A dye layer having first and second facial surfaces, the first facial surface of the dye layer in direct contact with the second facial surface layer, the dye layer comprising a polymer resin and a dye in which the polymer resin has a weight average molecular weight of 5,000 to 1,000,000 grams per mole and a Tg of greater than 25° C. and the dye soluble in each of (i) an organic solvent, (ii) the polymer resin of both the dye and timing layers, and (iii) the plasticizer of the activating layer, the dye present in the dye layer at a concentration of 1-30 parts solids based on the total solids of the dye layer, and
7. A substrate having first and second facial surfaces, the first facial surface of the substrate in direct contact with the second facial surface of the dye layer, the substrate inert to the plasticizer of the activating layer.

In one embodiment the dye of dye layer 6 is soluble in the solvent. In one embodiment dye particles are dispersed in a solvent with an insoluble resin binder. In one embodiment the second section of the kit further comprises a pressure sensitive adhesive (PSA) layer for mounting the second section to a substrate. In one embodiment the second section further comprises a release liner to protect the PSA layer. In one embodiment the timing layer is not tacky and is without the release sheet of 4. In one embodiment the timing layer is not tacky but is contact with the optional release sheet of 4 (to keep it clean until ready for use). In one embodiment the timing layer is tacky and is in contact with the optional release sheet of 4.

BRIEF DESCRIPTION OF THE DRAWINGS

The invention is described generally with reference to the drawings for the purpose of illustrating certain embodiments only, and not for the purpose of limiting the scope of the invention. In the drawings like numerals are used to designate like parts throughout the same.

DETAILED DESCRIPTION OF THE PREFERRED EMBODIMENT

Definitions

Figure 1:
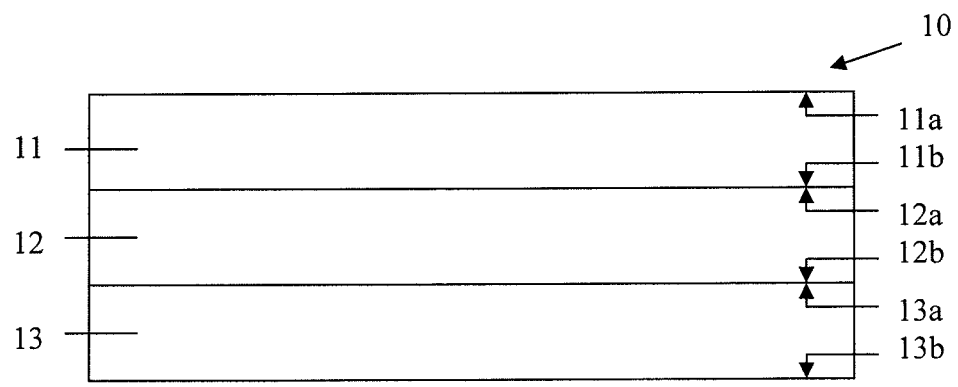
FIG. 1 is a schematic representation of a first section of one embodiment of a time indicator of this invention.

Unless stated to the contrary, implicit from the context, or customary in the art, all parts and percents are based on weight and all test methods are current as of the filing date of this disclosure. For purposes of United States patent practice, the contents of any referenced patent, patent application or publication are incorporated by reference in their entirety (or its equivalent US version is so incorporated by reference) especially with respect to the disclosure of definitions (to the extent not inconsistent with any definitions specifically provided in this disclosure) and general knowledge in the art.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, layer thickness, is from 100 to 1,000, then all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, the label and layer thicknesses.

"Facial surface" and like terms are used in distinction to "edge surface". For example, if rectangular in shape or configuration, a layer, e.g., film, will comprise two opposing facial surfaces joined by four edge surfaces (two opposing pairs of edge surfaces, each pair intersecting the other pair at right angles). If circular in configuration, then the layer will comprise two opposing facial surfaces joined by one continuous edge surface.

"Permeable" and like terms describes a material, e.g., a film, filter, absorbent, scrim, etc., through which a fluid, e.g., a gas, can pass under normal use conditions. "Nonpermeable" and like terms describes a material, e.g., an adhesive, film, etc., through which a fluid cannot pass under normal use conditions.

"Ink" and like terms mean a coatable or printable formulation that can and usually does contain a dye and/or pigment.

"Dye" and like terms mean a light absorbing compound that is present in a molecularly dispersed (dissolved) form.

"Pigment" and like terms mean a visible light reflecting or absorbing material or compound that is present in a non-molecularly dispersed (particulate) form.

"Graphic", "graphic image" and like terms mean text or pictorial representations formed of ink or other dye or pigment substances. Graphics include, but are not limited to, words, numbers, bar codes, pictures, designs (geometric or otherwise), and solid colors (typically applied by flood coating).

"Reflective substance" and like terms mean an electromagnetic energy reflective material or compound that is present in a molecularly dispersed or dissolved form. "Reflective" as used in this definition is a function of opacity as defined in ASTM D2805.

"Appearance" and like terms mean readable by the unaided human eye or by machine.

First Section of the Time Indicator

Topsheet

The topsheet of the time indicator of this invention is sufficiently translucent so that a graphic or color beneath it is visible to the naked eye under typical viewing conditions, e.g., daylight or the ambient light available in a typical artificially lit room such as an office or store. The topsheet can be clear or tinted, and preferably it is transparent. The topsheet can comprise indicia, e.g., a preprinted graphic such as the word "EXPIRED" OR "VOID", that is visible by machine or to the naked eye under typical viewing conditions only after the timing layer has expired.

The topsheet can comprise any polymeric material that is sufficiently translucent that it does not significantly detract from the visibility of the dye. Typically the topsheet is a polymeric film, e.g., a film comprising a polyolefin such as polyethylene or polypropylene, or polyester such as polyethylene terephthalate (PET), or the like. The thickness of the topsheet, also known as an overlay substrate or cover sheet, is a function of a number of different variables including but not limited to the design thickness of the indicator, degree of protection desired for the underlying graphic, cost, and the like, but typically the thickness is from 0.5 to 6 mil (0.0127 to 0.1524 millimeters (mm)), more typically from 1 to 3 mil (0.0254 to 0.0762 mm).

The topsheet comprises first and second facial surfaces with the first facial surface exposed or open to the environment and the second facial surface in contact with a facial surface of the activating layer.

In one embodiment the topsheet can be covered with an optional, translucent topcoat which is printable by any convenient manner, e.g. direct thermal, thermal transfer, dot-matrix, inkjet, or handwriting using pens, pencils or markers. Topcoat formulations are commercially available and well known in the art. Examples include 159TT and 334M (both available from Actega Wit) which are a thermal transfer receptive and writable topcoat, respectively. Typically, the formulations are urethane or acrylate based formulations and applied in a thickness range of 2-10 microns.

Activating Layer

The activating layer, also known as the activation or enhancement layer, is typically colorless and comprises a plasticizer and a polymer resin. The plasticizer, also known as a migrating agent, is compatible, i.e., soluble, with the dye of the dye layer and the resin of the timing layer. Monomeric and polymeric plasticizers can be use, and these plasticizers include but are not limited to PLASTHALL® P-550 (a polyester glutarate), PLASTHALL® 7050 (a dialkyl diether glutarate), PLASTHALL® TOTM (trioctyl trimellitate), and PARAPLEX® G-25 (a polyester sebacate), all available from The HallStar Company.

Any film-forming polymer resin that can be solubilized by the selected plasticizer can be used in the activating layer, and representative polymer resins include, but are not limited to, polyurethane, polyester, natural or synthetic rubber, rubber-acrylic hybrid, polyamide, polyethylene-vinyl acetate, acrylic, and the like, with polyurethane resins preferred. The weight average molecular weight (Mw) of the resin can vary widely, but it is typically between 5,000 and 1,000,000, more typically between 10,000 and 40,000, grams per mole for thermoplastic polyurethane.

The plasticizer is admixed with the resin to lower the glass transition temperature (Tg) of the resin and, in turn, increase the adhesive property of the resin. Typically, the activating layer comprises 20 to 80, more typically 40 to 60, weight percent of the plasticizer. In a preferred embodiment, utilizing a non-pressure sensitive polymer resin, such as ESTANE 5703 from Lubrizol, allows for the incorporation of higher loadings of plasticizer to enhance the migration of the dye. Typically, the remainder of the layer comprises the polymer resin although the layer can comprise other components as well, e.g., antioxidants, UV-inhibitors, etc., but these other components are typically used in nominal amounts, e.g., less than 2, more typically less than 1, wt % of the activating layer. Tackifying agents known to the art can be added to increase adhesion to the timing layer surface. Typically, the amount of tackifying agent ranges from 1 to 30 parts based on total solids.

The thickness of the activating layer is, like the thickness of the topsheet, a function of a number of different variables including but not limited to the desired timing, design thickness of the indicator, the nature and amount of plasticizer, the nature of the polymer resin, cost and the like, but typically the thickness is from 0.2 to 3 mil (0.00508 to 0.0762 mm), more typically from 0.5 to 1.5 mil (0.0127 to 0.0381 mm). The activating layer comprises first and second facial surfaces with the first facial surface in contact with the second facial surface of the topsheet and the second facial surface, depending upon the state of the time indicator, covered with a protective or release layer, open to the environment, or in contact with a facial surface of the timing layer.

Topsheet and Activating Layer

The activating layer in combination with the topsheet comprises the first section of the time indicator. This first section is typically manufactured separate from the second section of the time indicator, and it typically comprises an optional release layer to protect the activating layer during manufacturing, packaging, storage and/or shipping. The topsheet and activating layer can be joined to one another in any convenient manner with or without the use of an adhesive. Typically, the two layers are joined to one another without the use of an adhesive using any one of a number of known coating processes. When the time indicator is to be activated, the optional release layer in contact with the second facial surface of the activating layer is removed so that the second facial surface of the activating layer can be brought into contact with the first facial surface of the timing layer. Exemplary release layers include, but are not limited to, polyvinyl alcohol, silicones, fluorinated chemicals, glassine paper and waxes.

Second Section of the Time Indicator

Timing Layer

The timing layer comprises a polymer resin and a pigment. Like the activating layer, any film-forming polymer resin can be used for the timing layer, and representative polymer resins include, but are not limited to, acrylic, polyurethane, polyester and the like, with polyurethane and polyester resins preferred. The weight average molecular weight (Mw) of the resin can vary widely, and it is typically between 5,000 and 1,000,000, more typically between 10,000 and 40,000, grams per mole for thermoplastic copolyester. The resin has a glass transition temperature (Tg) typically greater than 25° C., more typically greater than 50° C., which maximizes the storage stability of the final construction with the preferred Tg range determined in large part by the chemical composition of the timing layer.

The pigment can be any reflective, opaque, or absorptive substance such as aluminum, stainless steel, natural and synthetic mica, coated glasses, metal oxides, silicates, bismuth oxychloride, calcium carbonate, barium sulfate, carbon black but is typically and preferably aluminum flake and/or titanium dioxide ($TiO_2$). Aluminum flake is a preferred pigment because its high reflectivity and opacity reduces the visibility of the dye as it migrates through the timing layer, minimizing the grey time or, in other words, the time that exists between the start of color development to the completion of the color development (both as observed by a machine or the unaided eye). For example, a preferred, film-forming timing layer that is constructed using equal parts of either $TiO_2$ or aluminum flake has an opacity of 82% and 100%, respectively, per ASTM D2805. The $TiO_2$ containing construction will appear pink prior to activation due to low opacity while the aluminum flake containing construction will have no pink color.

The thickness of the timing layer is, like the thickness of the topsheet and activating layer, a function of a number of different variables including but not limited to the desired timing, design thickness of the time indicator, the nature and amount of pigment, the nature of the polymer resin, cost and the like, but typically the thickness is from 0.2 to 3 mil (0.00508 to 0.0762 mm), more typically from 0.5 to 1.5 mil (0.0127 to 0.0381 mm). The timing layer comprises first and second facial surfaces with the first facial surface, depending upon the state of the time indicator, covered with a protective or release layer, open to the environment, or in contact with the facial surface of the activating layer. The second facial surface of the timing layer is in contact with the first facial surface of the dye layer.

Surprisingly, the use of aluminum flake allows for one to reduce the thickness of the timing layer to achieve multi-day timing due to its inherently high opacity. Furthermore, the reduced thickness allows the timing layer to be printed using processes known to the art (e.g. gravure, flexo, etc.). This allows for the application of multiple timing layers in a single construction (see FIG. 5).

The timing layer can comprise indicia, e.g., a preprinted graphic such as the word "EXPIRED" or "VOID", that is visible by machine or to the naked eye under typical viewing conditions only after the timing layer has expired.

Dye Layer

The dye layer comprises a polymer resin and an organic solvent soluble dye. Like the activating and timing layers, any film-forming polymer resin can be used for the dye layer, and representative polymer resins include, but are not limited to, acrylic, polyurethane, polyester, polyvinyl chloride, rubber, rubber-acrylic hybrid and the like, with polyurethane and polyester resins preferred. The weight average molecular weight (Mw) of the resin can vary widely, and it is typically between 5,000 and 1,000,000, more typically between 10,000 and 40,000, grams per mole for thermoplastic polyester. The resin has a Tg typically greater than 25° C., more typically greater than 50° C. which maximizes the storage stability of the final construction, with the preferred Tg range determined in large part by the chemical composition of the film substrate. An alternative method would be to solubilize the dye in a pressure sensitive adhesive.

The dye component of the dye layer is water-insoluble and soluble in organic solvents such as nonpolar solvents such as various aromatic and aliphatic hydrocarbons like toluene, xylene, pentane, etc., and various polar solvents such as ketones, acetates, ethers, esters, alcohols, etc. The dye is also soluble in the resin and plasticizer of the activating layer. A wide variety of dyes can be used in the practice of this invention including diazo dyes, carbonyl dyes, polymethine dyes, azomethine dyes, triarylmethane dyes, indoaniline dyes, indophenol dyes, xanthine dyes, oxazine dyes, and thiazine dyes although the dyes of the anthraquinone, methine and azo dye families are preferred. The dyes are typically used at a concentration of 1-30 parts, preferably 10-25 parts solids in the dye layer. The thickness of the dye layer is, like the thickness of the topsheet, activating and timing layers, a function of a number of different variables including but not limited to the design thickness of the time indicator, the nature and amount of pigment, the nature of the polymer resin, cost and the like, but typically the thickness is from 0.001 to 1 mil (0.0000254 to 0.0254 mm), more typically from 0.05 to 0.2 mil (0.00127 to 0.00508 mm). Solubilizing the dye in an organic solvent makes it more uniformly available to the solubilizing action of the plasticizer than if it was in a particulate or dispersed form, such as solvent soluble dye particulates dispersed in a water based coating.

The dye layer can comprise indicia, e.g., a preprinted graphic such as the word "EXPIRED" or "VOID", that is visible by machine or to the naked eye under typical viewing conditions only after the timing layer has expired.

Base Substrate Layer

The base of the time-indicator can be any substrate, typically a film or paper, whose structural integrity is not compromised or otherwise affected by the plasticizer. Exemplary substrate layers include, but are not limited to, various polymeric films such as polyesters, polyimides, polyolefins, polycarbonates, various nonpolymeric materials such as glassine or wax paper, woven and non-woven papers or fabrics, and metal foils. In one embodiment, the preferred substrate is a solvent resistant polymeric film that will provide a uniform, smooth surface for the dye and timing layers which will improve the consistency and accuracy of dye migration after activation.

Timing Layer, Dye Layer and Substrate

The dye layer needs to adhere to the base substrate, and it is typically applied to the base substrate using a printing or coating technique, e.g., flexographic, gravure, screen, Meyer rod or the like. Typically, the polymer resin chemistry of the timing and dye layers is the same which provides good adhesion and minimizes the interface between the two layers through which the plasticizer needs to migrate. The timing layer can be applied to the dye layer in any convenient manner but is typically applied by means of heat lamination and without the use of an adhesive. If heat lamination is chosen as the method for applying the dye layer, proper selection of processing controls such as lamination temperature, roller speed and pressure are necessary to control and minimize the migration of the dye into the timing layer, and this selection is well within the knowledge of those skilled in the art. Similar to the activating layer, the timing layer can be protected by an optional release liner until the second section of the time indicator is ready to be joined to the first section of the time indicator. In certain constructions of the time indicator, the first and second sections are joined together by a common release liner separating the activating and timing layers. When ready for use, the two sections are separated from the common release liner, and then joined together, typically by pressing the open surface of the activating layer against the open surface of the timing layer to form an activated time indicator.

Specific Embodiments

FIG. 1 is a schematic representation of a first section of one embodiment of a time indicator of this invention. First section 10 (also known as an activation section) comprises topsheet 11 and activating layer 12. Topsheet 11 comprises first and second facial surfaces 11a and 11b, and activating layer 12 comprises first and second facial surfaces 12a and 12b, with second facial surface 11b of topsheet 11 in direct contact with first facial surface 12a of activating layer 12. In one embodiment, first section 10 further comprises optional release sheet or layer 13 which comprises facial surfaces 13a and 13b in which facial surface 13a is in direct contact with facial surface 12b of activating layer 12. The purpose, of course, of optional release sheet 13 is to protect activating layer 12 until it is ready to be joined to the timing layer to activate the time indicator.

Figure 2:
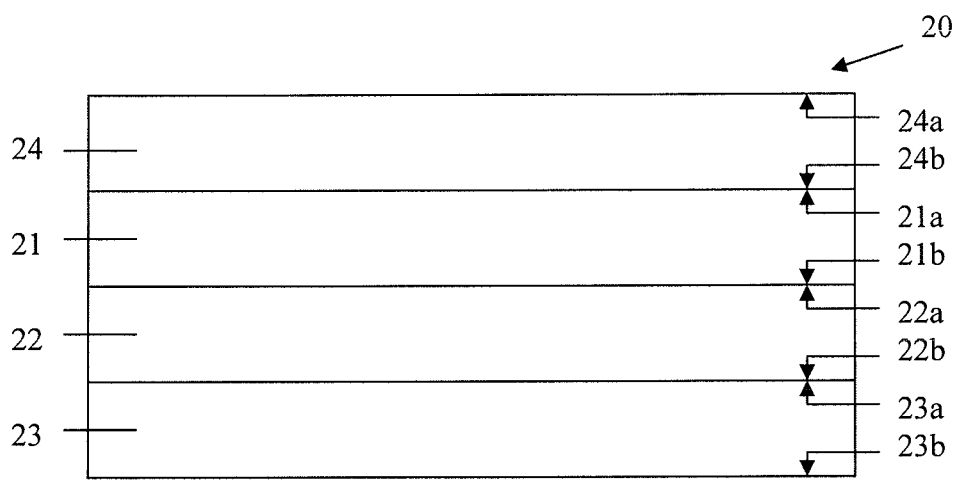
FIG. 2 is a schematic representation of a second section of one embodiment of a time indicator of this invention.

FIG. 2 is a schematic representation of a second section of one embodiment of a time indicator of this invention. Second section 20 (also known as a base layer) comprises timing layer 21, dye layer 22 and substrate 23. Timing layer 21 comprises first and second facial surfaces 21a and 21b, dye layer 22 comprises first and second facial surfaces 22a and 22b, and substrate 23 comprises first and second facial surfaces 23a and 23b. Second facial surface 21b of timing layer 21 is in direct contact with first facial surface 22a of dye layer 22, and second facial surface 22b of dye layer 22 is in direct contact with first facial surface 23a of substrate 23. In one embodiment, second section 20 further comprises optional release sheet or layer 24 which comprises facial surfaces 24a and 24b in which facial surface 24b is in direct contact with facial surface 21a of timing layer 21. The purpose of optional release sheet 24 is like that for release sheet 13, i.e., to protect timing layer 21 until it is ready to be joined to the activating layer to activate the time indicator.

Figure 3:
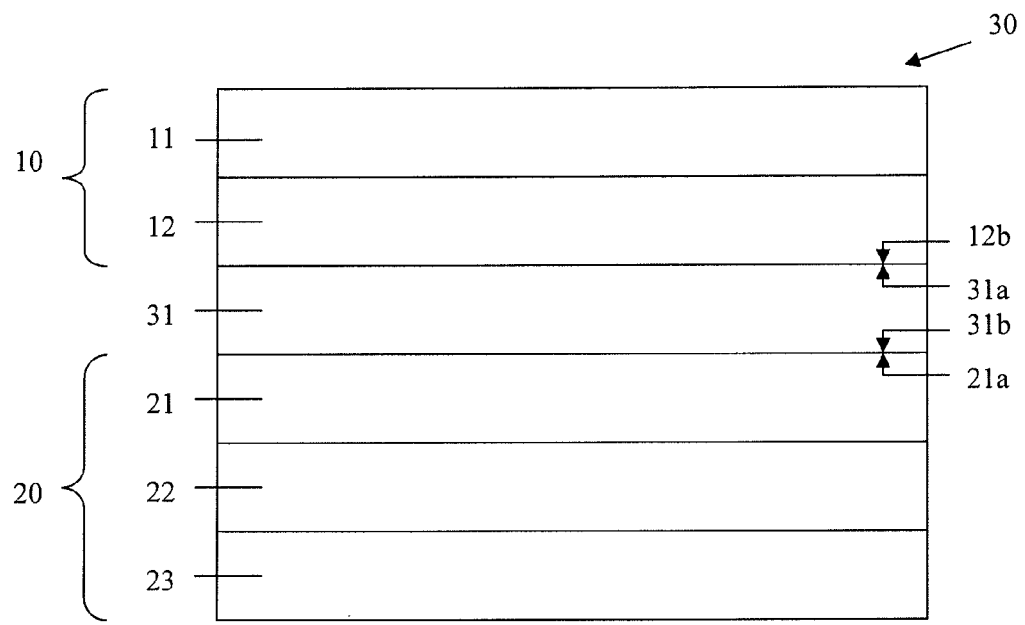
FIG. 3 is a schematic representation of one embodiment of a time indicator in which the first and second sections are joined to one another but the time indicator is not activated.

FIG. 3 is a schematic representation of one embodiment of a time indicator in which the first and second sections are joined to one another but the time indicator is not activated. In this embodiment time indicator 30 comprises first section 10 joined to second section 20 by release sheet 31 which comprises first facial surface 31a and second facial surface 31b. First facial surface 31a of release sheet 31 is in direct contact with second facial surface 12b of activating layer 12 while second facial surface 31b is in direct contact with first facial surface 21a of timing layer 21. Release sheet 31 is constructed from materials of any typical release sheet, e.g., polymeric film, glassine paper, etc., that not only protects the integrity of both the activating and timing layers, but also does not allow a component bleed from one layer to the other layer and thus initiating a pre-mature activation of the time indicator.

Figure 4:
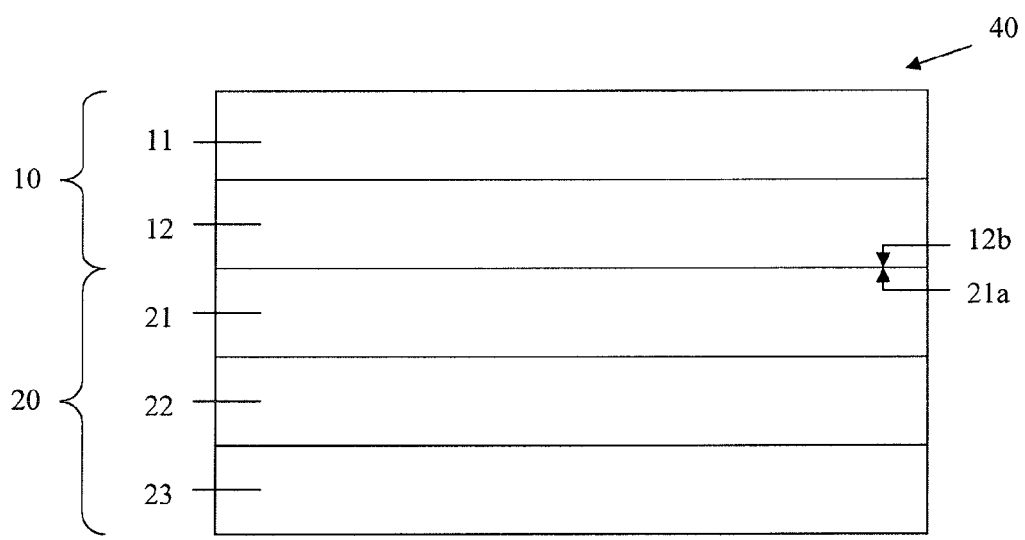
FIG. 4 is a schematic representation of one embodiment of an activated time indicator.

FIG. 4 is a schematic representation of one embodiment of an activated time indicator. Activated time indicator 40 comprises first section 10 joined to second section 20 at the interface of activating layer 10 and timing layer 21, i.e., at the interface formed by the direct contact of second facial surface 12b of activating layer 12 and first facial surface 21a of timing layer 21. The embodiment of FIG. 4 is essentially the embodiment of FIG. 3 without release sheet 31 separating the first and second sections of the time indicator.

Figure 5:
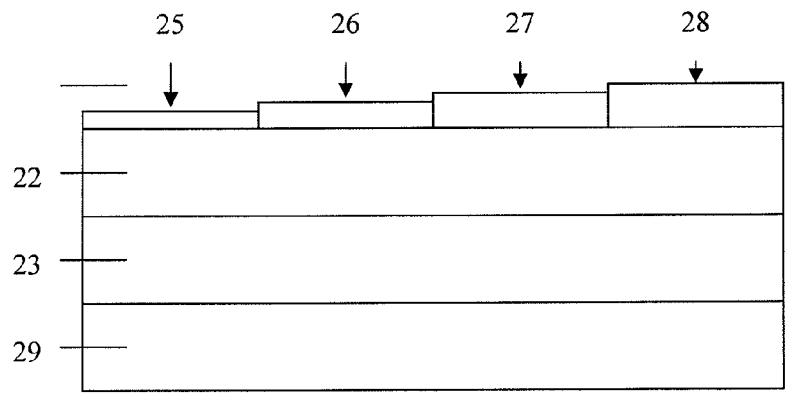
FIG. 5 is a schematic of the second section of one embodiment of a time indicator of this invention coated with multiple timing layers.

FIG. 5 is a schematic of an alternative second section of one embodiment of a time indicator of this invention in which multiple timing layers are coated onto a dye layer. Second section 20 (also known as a base layer) contains multiple timing layers 25, 26, 27 and 28 that are applied to dye layer 22. The embodiment of FIG. 5 is essentially the embodiment of FIG. 2 with multiple time layers 25, 26, 27 and 28 applied to the surface of the dye layer 22. Timing layer 25, 26, 27 and 28 are different thicknesses. These multiple time layers allow for multiple indication zones to be located on a single time indicating construction. Layer 23 is the substrate layer, and layer 29 is an optional adhesive layer.

Activation of the time indicator is essentially the joining of the first and second sections. In the embodiment in which each section is manufactured as a separate piece with an optional, protective release sheet or liner such as described in FIGS. 1 and 2, the release sheet is simply removed from both sections, e.g., typically by peeling it off the layer to which it is adhered, discarding the removed release liners in an environmentally acceptable manner, and then joining the first and second sections to one another, e.g., simply by laminating the activating layer to the timing layer. The plasticizer or migrating agent of the activating layer will move through the timing layer to mobilize the dye in the dye layer which will then migrate into and through the timing layer in which it will become visible. Alternatively, release sheet 31 is removed from time indicator 30, and sections 10 and 20 are then joined to one another to activate the time indicator.

Example 1

Activating Layer

A monomeric plasticizer (PLASTHALL® 7050 available from HallStar), 4.7 g, and a 25% solution of a polyester type polyurethane (ESTANE® 5703 available from Lubrizol), in methyl ethyl ketone 75 g, was placed into a glass jar. The solution was mixed on a roller for 30 minutes to create a homogenous solution.

The above monomeric plasticizer solution was coated onto a 2.0 mil polyester film using a roll coating method that consisted of two stainless steel rollers that have an adjustable gap between the two. The coated film was placed into a 300° F. (149° C.) oven for 1 minute to drive off solvent. A silicone coated release liner was placed over the adhesive. The thickness of the coating was 1.0 mil after solvent removal.

Timing Layer

A 70% dispersion of titanium dioxide in methyl ethyl ketone (prepared by ball milling titanium dioxide, 70 g, methyl ethyl ketone, 28 g and a dispersing additive (DISPER-BYK® 111 available from Altana, 2 g, for 24 hours), 66.4 g, a 35% solution of an acrylic resin in methyl ethyl ketone (ELVACITE® 2016 available from Lucite International, Inc.), 132.8 g, a dispersing additive (DISPERBYK® 111), 0.95 g, and a silicone leveling agent (BYK® 302 available from Altana), 0.3 g, were added to a glass jar and mixed for 24 hours on a roller.

The above formulation was coated onto a silicone coated release liner using a roll coating method that consisted of two stainless steel rollers that have an adjustable gap between the two. The coated film was placed into a 300° F. (149° C.) oven for 4 minutes to drive off solvent yielding a dry film thickness of 0.75 mils.

Dye Layer

A solvent soluble dye (MACROLEX® Red H available from Lanxess), 2.0 g, and a 35% solution of an acrylic resin (ELVACITE® 2016) in methyl ethyl ketone, 50 g, were added to a glass jar and mixed for 30 minutes on a roller.

The above formulation was coated onto a polyester film base sheet using a roll coating method that consisted of two stainless steel rollers that have an adjustable gap between the two. The coated film was placed into a 300° F. (149° C.) oven for 3 minutes to drive off solvent. The dry thickness of the coating was 0.10 microns.

Timing Layer/Dye Layer Construction

The timing layer and dye layer were heat laminated together to create a single construction. The laminating temperature used (180° F. (82° C.)) was higher than the glass transition temperature of the polymers chosen for the timing and dye layers to ensure good adhesion between the timing layer and the dye layer. For Example 1 and all subsequent examples the same roller speed, temperature and pressure was chosen during heat lamination to keep the amount of dye transfer into the timing layer consistent. Increasing or decreasing the speed during heat lamination will effect the distance the dye will transfer into the timing layer.

Example 2

Activating Layer

The activating formulation and coating method was the same as described in Example 1 except the amount of monomeric plasticizer (PLASTHALL® 7050) was increased to 12.5 g.

Timing Layer

The timing formulation and coating method used was the same as described in Example 1 except the dry thickness was 0.50 mil.

Dye Layer

The dye formulation and coating method used was the same as described in Example 1.

Example 3

Activating Layer

The activating formulation and coating method used was the same as described in Example 2.

Timing Layer

The timing formulation and coating method used is the same as described in Example 1.

Dye Layer

The dye formulation and coating method used is the same as described in Example 1.

Example 4

Activating Layer

The activating formulation and coating method used was the same as described in Example 2.

Timing Layer

The timing formulation and coating method used was the same as described in Example 1 except the dry thickness was 1.00 mil.

Dye Layer

The dye formulation and coating method used is the same as described in Example 1.

Example 5

Activating Layer

The activating formulation and coating method was the same as described in Example 2 except the amount of monomeric plasticizer (PLASTHALL® 7050) was increased to 18.75 g.

Timing Layer

The timing formulation and coating method used is the same as described in Example 1.

Dye Layer

The dye formulation and coating method used is the same as described in Example 1.

Example 6

Activating Layer

The activating formulation and coating method used was the same as described in Example 5 except the thickness was 1.4 mil.

Timing Layer

Titanium dioxide, 17 g, a dispersing additive (DISPER-BYK® 111 available from Altana), 2 g, a 30% solution of a polyester resin (VYLON® 103 available from Toyobo) in a 50:50 blend of methyl ethyl ketone and toluene, 132.8 g, and a silicone leveling agent (BYK® 333 available from Altana), 0.3 g, were added to a glass jar and ball milled for 24 hours on a roller.

The above formulation was coated onto a silicone coated release liner using a roll coating method that consisted of two stainless steel rollers that have an adjustable gap between the two. The coated film was placed into a 300° F. (149° C.) oven for 4 minutes to drive off solvent. The thickness of the dry film was varied, depending on the gap between the two rollers.

Dye Layer

A solvent soluble dye (MACROLEX® Red H), 1.32 g, and a 30% solution of an a polyester resin (VYLON® 103) in methyl ethyl ketone, 25 g, were added to a glass jar and mixed for 30 minutes on a roller.

The above formulation was coated onto a polyester film base sheet using a roll coating method that consisted of two stainless steel rollers that have an adjustable gap between the two. The coated film was placed into a 300° F. (149° C.) oven for 3 minutes to drive off solvent. The dry thickness of the coating was 0.10 microns.

Example 7

Activating Layer

The activating formulation and coating method used was the same as described in Example 6.

Timing Layer

The timing formulation and coating method used was the same as described in Example 6 except an aluminum flake (SPARKLE SILVET®ULTRA 0011-20-P available from Silberline) was used as the pigment instead of $TiO_2$.

Dye Layer

The dye formulation and coating method used was the same as described in Example 6.

Example 8

Activating Layer

The activating formulation and coating method used was the same as described in Example 6.

Timing Layer

The timing formulation and coating method used was the same as described in Example 7 except the thickness was 0.75 mil.

Dye Layer

The dye formulation and coating method used was the same as described in Example 6.

Example 9

Activating Layer

The activating formulation and coating method used was the same as described in Example 6.

Timing Layer

The timing formulation and coating method used was the same as described in Example 7a different polyester resin (Vylon® 240 available from Toyobo) was used.

Dye Layer

The dye formulation and coating method used was the same as described in Example 6

Example 10

Activating Layer

The activating formulation and coating method used was the same as described in Example 6.

Timing Layer

The timing formulation and coating method used was the same as described in Example 9 except the final thickness was 0.75 mil.

Dye Layer

The dye formulation and coating method used was the same as described in Example 6.

Example 11

Activating Layer

The activating formulation and coating method used was the same as described in Example 6.

Timing Layer

The timing formulation and coating method used was the same as described in Example 7 except aluminum flake (SILVERSTAR 009 available from Silberline) was used as the pigment.

Dye Layer

The dye formulation and coating method used was the same as described in Example 6.

Example 12

This is a commercially available 1 day time indicating device available from Brady Worldwide Corporation (TEMPbadge® 1 day expiring TIMEbadge).

Timing Experiments

Activation of timing was achieved by applying the activating layer onto the timing layer surface of the timing layer/dye layer construction. The appearance and intensity of color was monitored as a function of time using an X-Rite Series 530 Spectrophotometer, collecting quantitative color measurements such as image density (Magenta setting) and L*a*b* values (observer angle, 10°, illumination, D65). From the image density (M) values, the change in color intensity (ΔM) over time was relative to the initial color intensity value at t=0 hours. From the L*a*b* values, a delta E (ΔE) value was calculated using the CIE76 method. Reported below are the change in image density and ΔE as a function of time for various time indicator constructions. The following Table contains information related to time indicators constructed as described above.

Figure 6:
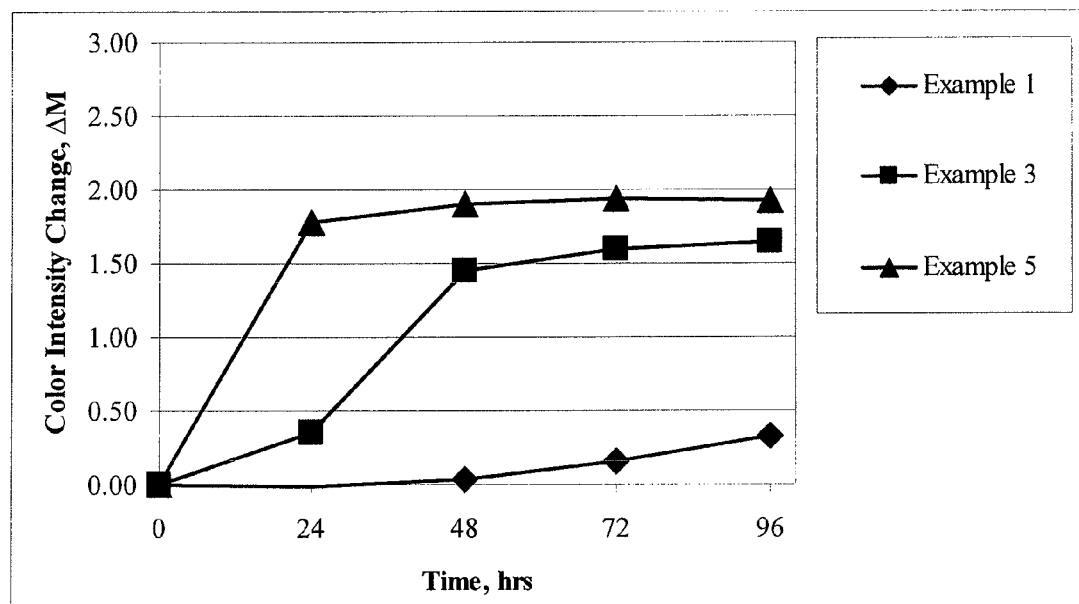
FIG. 6 is a line graph reporting the effect of increased plasticizer content within the activating layer on the change in color intensity ($\Delta M$) over time of Examples 1, 3 and 5.
Figure 7:
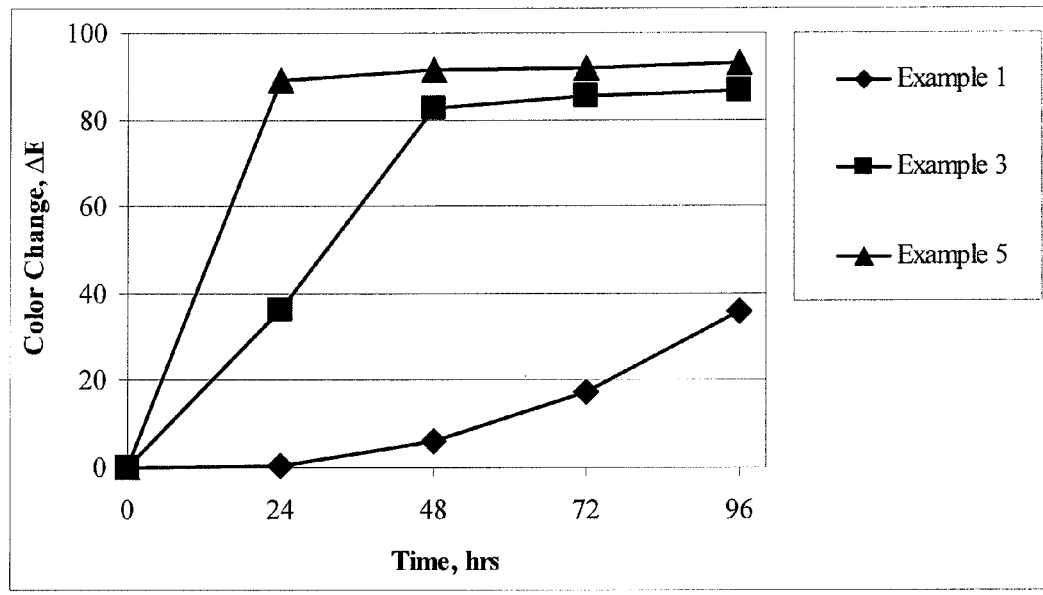
FIG. 7 is a line graph reporting the effect of increased plasticizer content within the activating layer on color change ($\Delta E$) over time of Examples 1, 3 and 5.

FIGS. 6 and 7 illustrate the effect of increased plasticizer content within the activating layer on the color development over time. Increasing the amount of plasticizer decreases the time at which color is first visible. In addition, high plasticizer content leads to higher intensities.

Figure 8:
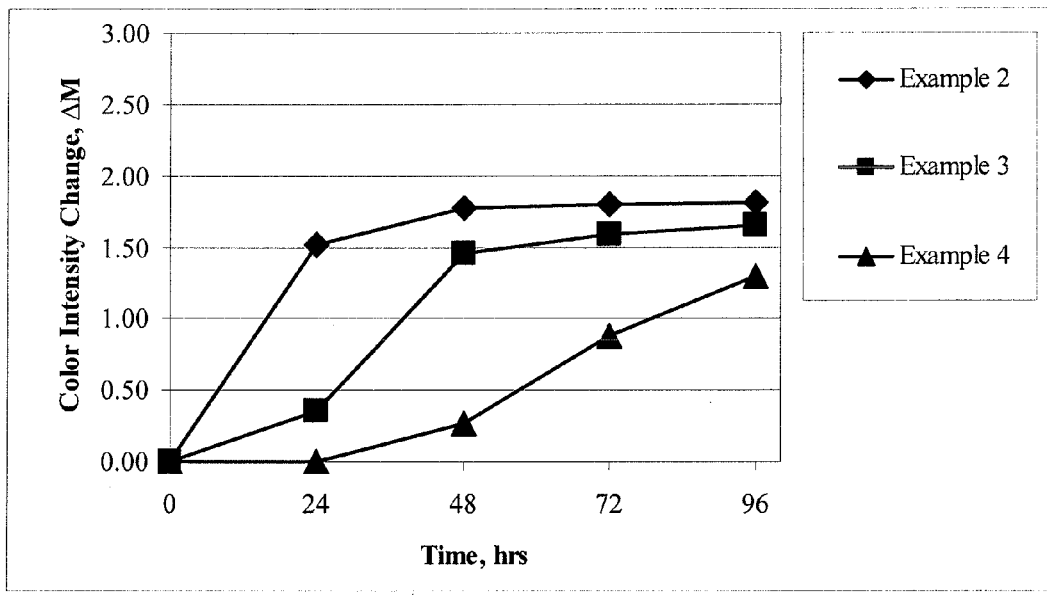
FIG. 8 is a line graph reporting the effect of increased timing layer thickness on the change in color intensity ($\Delta M$) over time of Examples 2, 4 and 6.
Figure 9:
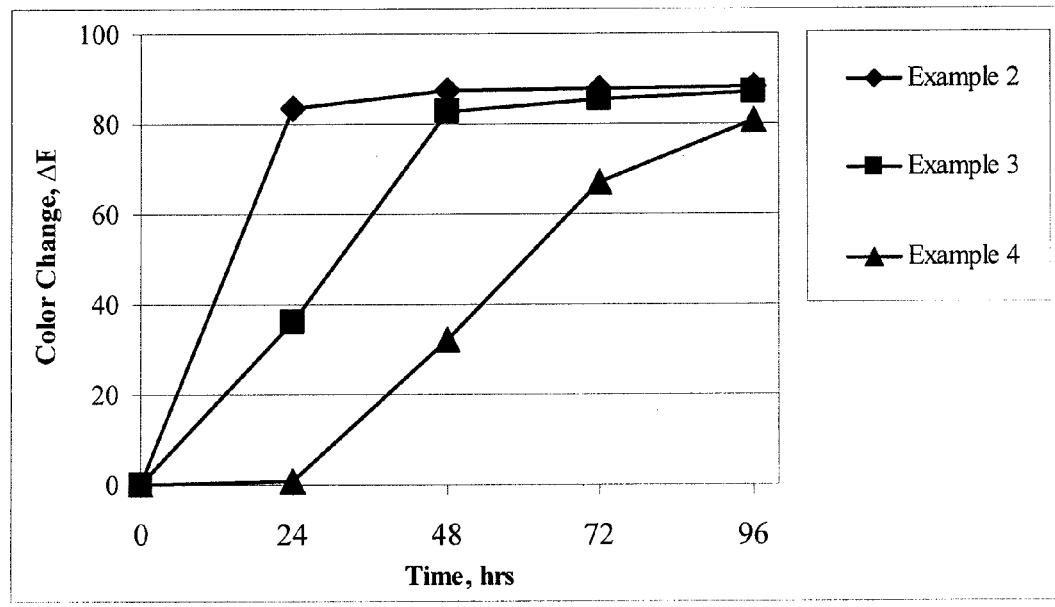
FIG. 9 is a line graph reporting the effect of increased timing layer thickness on color change ($\Delta E$) over time of Examples 2, 4 and 6.

FIGS. 8 and 9 illustrate the effect of increasing the timing layer thickness on color development over time. Increasing the thickness of the timing layer increases the time at which color is first visible.

Figure 10:
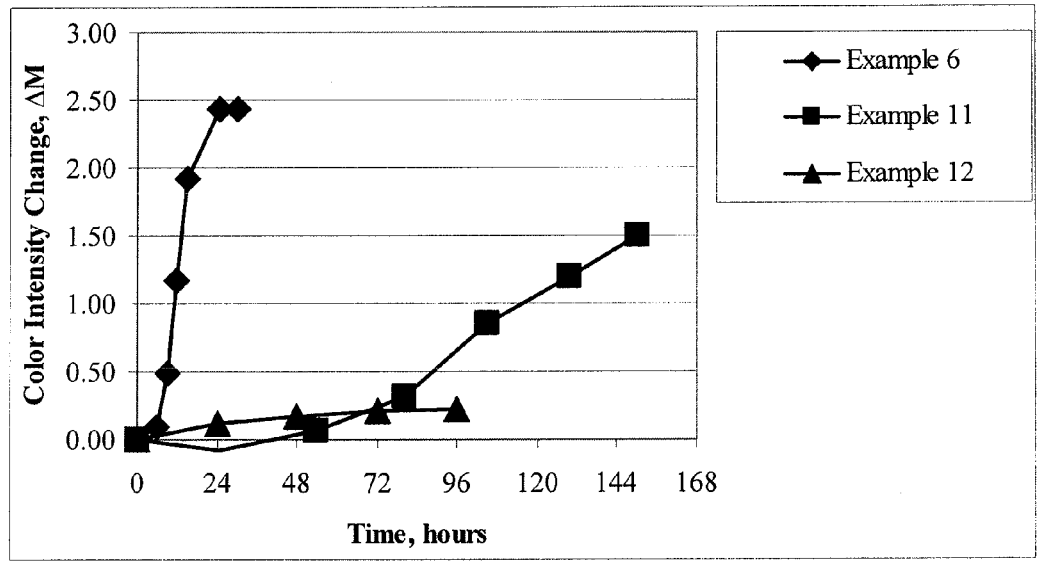
FIG. 10 is a line graph reporting the effect of different opacifying agents within the timing layer on the change in color intensity ($\Delta M$) over time of Examples 6, 11 and 12.
Figure 11:
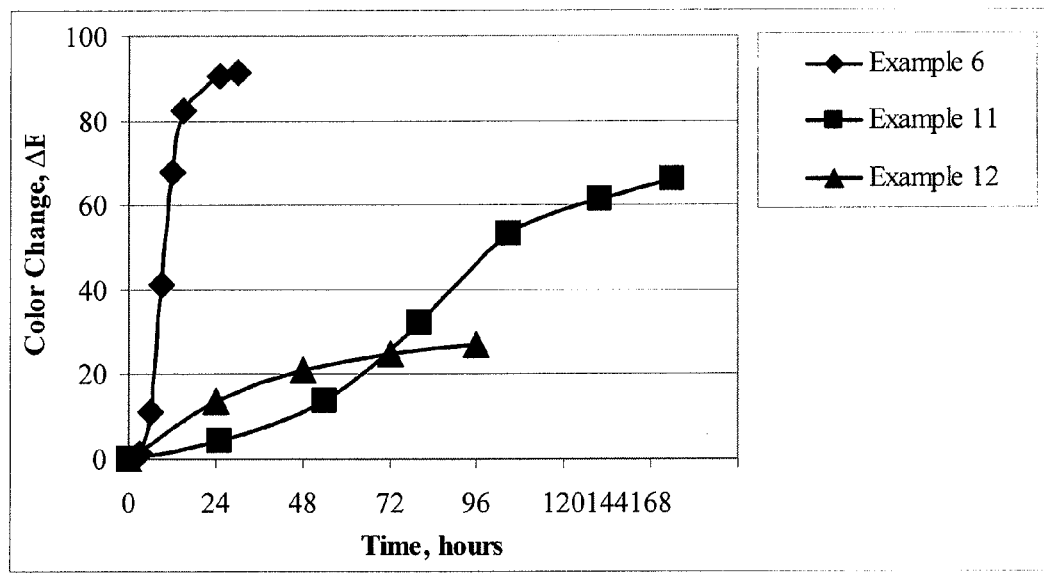
FIG. 11 is a line graph reporting the effect of different opacifying agents within the timing layer on color change ($\Delta E$) over time of Examples 6, 11 and 12.

FIGS. 10 and 11 illustrate the effect of using different opacifying agents within the timing layer on color development over time. For these examples, the content of the opacifying agent within the timing layer is constant. At these levels, the first development of color in $TiO_2$ occurs at an earlier time compared to aluminum flake. Examples 6 and 11 show the ability to control and extend the time indication using the increased opacity from the aluminum flake. Additionally, a comparison of the novel art with a commercially available time indicator is illustrated. Examples 6 and 11 show the greater color intensity that can be obtained versus a commercially available product (Example 12).

Figure 12:
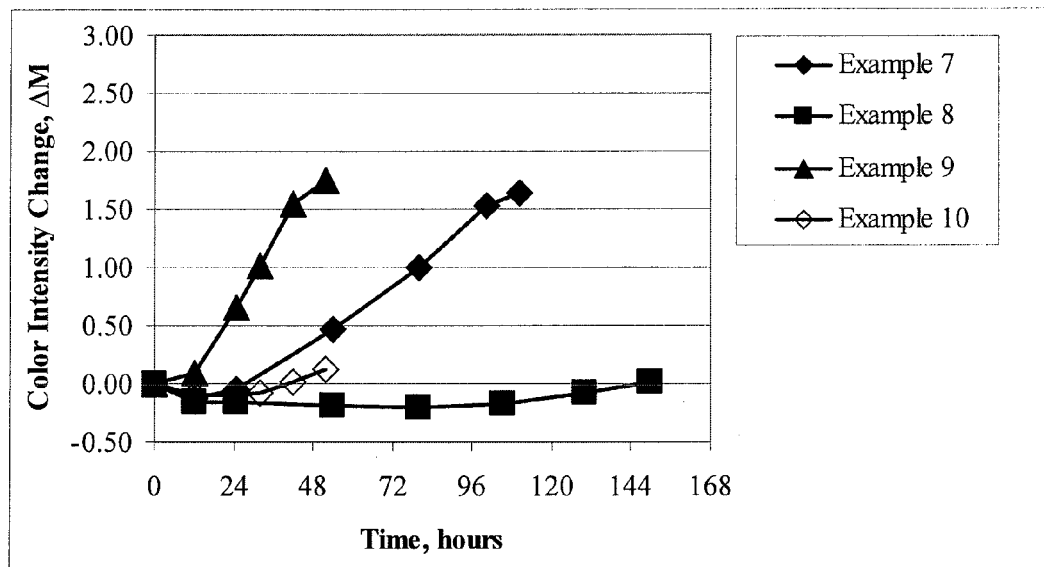
FIG. 12 is a line graph reporting the effect of different resins within the timing layer on the change in color intensity ($\Delta M$) over time of Examples 7, 8, 9 and 10.
Figure 13:
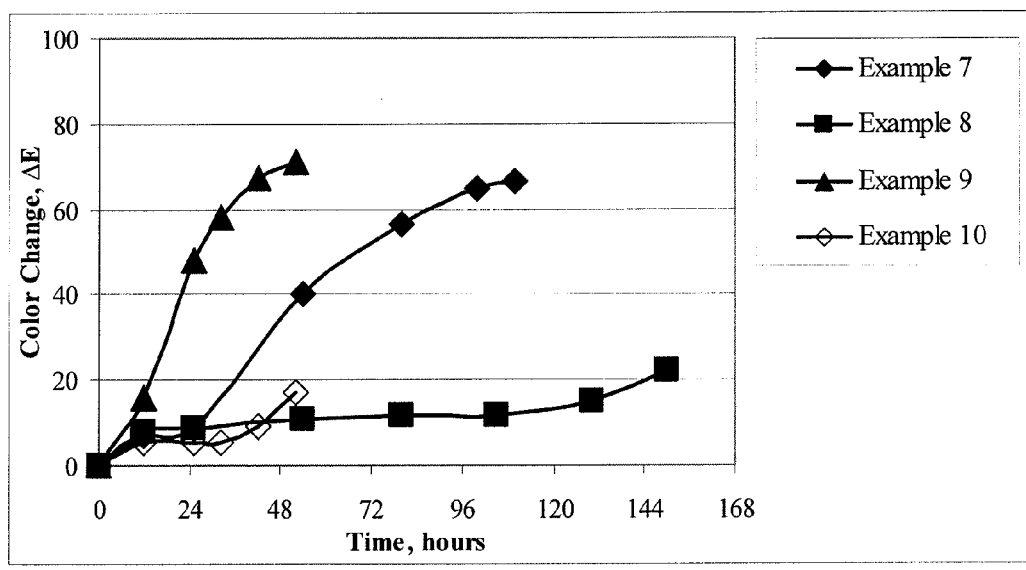
FIG. 13 is a line graph reporting the effect of different resins within the timing layer on the color change ($\Delta E$) over time of Examples 7, 8, 9 and 10.

FIGS. 12 and 13 illustrate the effect changing the type of resin that is used in the timing layer. These figures show the difference between two polyester resins used in the timing. The higher molecular weight resin (Vylon 103) extends the end point time compared to the lower molecular weight rein (Vylon 240). One skilled in the art could select a timing layer resin based upon the desired end timing point using the above with other parameters such as compatibility with the plasticizer and timing layer thickness.

Although the invention has been described with certain detail through the preceding description of the preferred embodiments, this detail is for the primary purpose of illustration. Many variations and modifications can be made by one skilled in the art without departing from the spirit and scope of the invention as described in the following claims.

TABLE

Time Indicator Construction

| | Activating Layer | | | Timing Layer | | | | Dye Layer | |
| | | | | Opacifying | | | | | |
| Ex. | Plasticizer content, % solids | Thickness, mils | Resin | Opacifying agent | agent content, % solids | Thickness, mils | Resin | Dye content, % solids | Timing + Dye Layer Opacity, % |
|---|---|---|---|---|---|---|---|---|---|
| 1 | 20 | 1.00 | Elvacite 2016 | TiO$_2$ | 50 | 0.75 | Elvacite 2016 | 10 | NR |
| 2 | 40 | 1.00 | Elvacite 2016 | TiO$_2$ | 50 | 0.50 | Elvacite 2016 | 10 | NR |
| 3 | 40 | 1.00 | Elvacite 2016 | TiO$_2$ | 50 | 0.75 | Elvacite 2016 | 10 | NR |
| 4 | 40 | 1.00 | Elvacite 2016 | TiO$_2$ | 50 | 1.00 | Elvacite 2016 | 10 | NR |
| 5 | 50 | 1.00 | Elvacite 2016 | TiO$_2$ | 50 | 0.75 | Elvacite 2016 | 10 | NR |
| 6 | 50 | 1.4 | Vylon 103 | TiO$_2$ | 23 | 0.50 | Vylon 103 | 15 | 82 |
| 7 | 50 | 1.4 | Vylon 103 | SilvetUltra 0011-20-P | 23 | 0.50 | Vylon 103 | 15 | 100 |
| 8 | 50 | 1.4 | Vylon 103 | SilvetUltra 0011-20-P | 23 | 0.75 | Vylon 103 | 15 | 100 |
| 9 | 50 | 1.4 | Vylon 240 | SilvetUltra 0011-20-P | 23 | 0.50 | Vylon 103 | 15 | 100 |
| 10 | 50 | 1.4 | Vylon 240 | SilvetUltra 0011-20-P | 23 | 0.75 | Vylon 103 | 15 | 100 |
| 11 | 50 | 1.4 | Vylon 103 | Silver Star 009 | 23 | 0.50 | Vylon 103 | 15 | 100 |

What is claimed is:

1. An activated, multilayer time indicator comprising:
    A. A translucent or transparent topsheet comprising a polymeric film having first and second facial surfaces,
    B. An activating layer having first and second facial surfaces, the first facial surface of the activating layer in contact with the second facial surface of the topsheet, the activating layer comprising a plasticizer and a polymer resin in which the plasticizer comprises 20-80 weight percent of the activating layer,
    C. A timing layer having first and second facial surfaces, the first facial surface of the timing layer in direct contact with the second facial surface of the activating layer, the timing layer comprising a polymer resin and a pigment in which the polymer resin has a weight average molecular weight of 5,000 to 1,000,000 grams per mole and a Tg of greater than 25° C., the polymer resin comprising 15-85 weight percent of the timing layer.
    D. A dye layer having first and second facial surfaces, the first facial surface of the dye layer in direct contact with the second facial surface of the timing layer, the dye layer comprising a polymer resin and a dye in which the polymer resin has a weight average molecular weight of 5,000 to 1,000,000 grams per mole and a Tg of greater than 25° C. and the dye soluble in each of an organic solvent, the polymer resin of both the dye and timing layers, and the plasticizer of the activating layer, the dye present in the dye layer at a concentration of 1-30 parts solids based on the total solids of the dye layer, and
    E. A substrate having first and second facial surfaces, the first facial surface of the substrate in direct contact with the second facial surface of the dye layer, the substrate inert to the plasticizer of the activating layer.

2. An inactivated, multilayer time indicator comprising:
    A. A translucent or transparent topsheet comprising a polymeric film having first and second facial surfaces,
    B. An activating layer having first and second facial surfaces, the first facial surface of the activating layer in contact with the second facial surface of the topsheet, the activating layer comprising a plasticizer and a polymer resin in which the plasticizer comprises 20-80 weight percent of the activating layer,
    C. A release sheet having first and second facial surfaces, the first facial surface of the release sheet in direct contact with the second facial surface of the activating layer, the release sheet a block to the migration of the plasticizer out of the activating layer,
    D. A timing layer having first and second facial surfaces, the first facial surface of the timing layer in direct contact with the second facial surface of the release sheet, the timing layer comprising a polymer resin and a pigment in which the polymer resin has a weight average molecular weight of 5,000 to 1,000,000 grams per mole and a Tg of greater than 25° C., the polymer resin comprising 15-85 weight percent of the timing layer,
    E. A dye layer having first and second facial surfaces, the first facial surface of the dye layer in direct contact with the second facial surface of the timing layer, the dye layer comprising a polymer resin and a dye in which the polymer resin has a weight average molecular weight of 5,000 to 1,000,000 grams per mole and a Tg of greater than 25° C. and the dye soluble in each of an organic solvent, the polymer resin of both the dye and timing layers, and the plasticizer of the activating layer, the dye present in the dye layer at a concentration of 1-30 parts solids based on the total solids of the dye layer, and
    F. A substrate having first and second facial surfaces, the first facial surface of the substrate in direct contact with the second facial surface of the dye layer, the substrate inert to the plasticizer of the activating layer.

3. A two-section, inactive, multilayer time indicator kit comprising:
    A. A first section comprising:
        1. A translucent or transparent topsheet comprising a polymeric file having first and second facial surfaces,
        2. An activating layer having first and second facial surfaces, the first facial surface of the activating layer in contact with the second facial surface of the topsheet, the activating layer comprising a plasticizer and a polymer resin in which the plasticizer comprises 20-80 weight percent of the activating layer, and
        3. A release sheet having first and second facial surfaces, the first facial surface of the release sheet in direct contact with the second facial surface of the activating layer, the release sheet a block to the migration of the plasticizer out of the activating layer, and
    B. A second section, separate and apart from the first section, comprising:
        4. A release sheet having first and second facial surfaces,
        5. A timing layer having first and second facial surfaces, the first facial surface of the timing layer in direct contact with the second facial surface of the release sheet, the timing layer comprising a polymer resin and a pigment in which the polymer resin has a weight average molecular weight of 5,000 to 1,000,000 grams per mole and a Tg of greater than 25° C., the polymer resin comprising 15-85 weight percent of the timing layer, 6. A dye layer having first and second facial surfaces, the first facial surface of the dye layer in direct contact with the second facial surface layer, the dye layer comprising a polymer resin and a dye in which the polymer resin has a weight average molecular weight of 5,000 to 1,000,000 grams per mole and a Tg of greater than 25° C. and the dye soluble in each of an organic solvent, the polymer resin of both the dye and timing layers, and the plasticizer of the activating layer, the dye present in the dye layer at a concentration of 1-30 parts solids based on the total solids of the dye layer, and 7. A substrate having first and second facial surfaces, the first facial surface of the substrate in direct contact with the second facial surface of the dye layer, the substrate inert to the plasticizer of the activating layer.

4. The multilayer time indicator of claim 1 in which the topsheet comprises a polyolefin or polyester and has a thickness of 0.5 to 6 mil (0.0127 to 0.1524 millimeters (mm)).

5. The multilayer time indicator of claim 1 or 2 in which the plasticizer of the activating layer is at least one of a polyester glutarate, a dialkyl diether glutarate, trioctyl trimellitate and a polyester sebacate, the polymer resin is at least one of polyurethane, polyester, rubber and rubber-acrylic hybrid with a weight average molecular weight (Mw) of 5,000 to 1,000,000, and the layer has a thickness is from 0.2 to 3 mil (0.00508 to 0.0762 mm).

6. The multilayer time indicator of claim 1 or 2 in which the polymer resin of the timing layer is at least one of polyurethane, polyester, acrylic, polyvinyl chloride the pigment of the timing layer is aluminum flake and/or titanium dioxide (TiO$_2$), and the layer has a thickness from 0.2 to 3 mil (0.00508 to 0.0762 mm).

7. The multilayer time indicator of claim 1 or 2 in which the polymer resin of the dye layer is at least one of polyurethane, polyester, acrylic, polyvinyl chloride, the dye of the dye layer is of the anthraquinone family, and the layer has a thickness from 0.001 to 1 mil (0.0000254 to 0.0254 mm).

8. The multilayer time indicator of claim 1 or 2 in which the substrate layer comprises a polymeric film or glassine paper.

9. The multilayer time indicator of claim 2 in which the release sheet comprises polyvinyl alcohol, a silicone, a fluorinated chemical, or a wax coated on a polymer film or glassine paper.

10. The multilayer time indicator of claim 1 or 2 further including a pressure sensitive adhesive with an optional protective liner backing.

11. The multilayer time indicator kit of claim 3 in which the topsheet comprises a polyolefin or polyester and has a thickness of 0.5 to 6 mil (0.0127 to 0.1524 millimeters (mm)).

12. The multilayer time indicator kit of claim 3 in which the plasticizer of the activating layer is at least one of a polyester glutarate, a dialkyl diether glutarate, trioctyl trimellitate and a polyester sebacate, the polymer resin is at least one of polyurethane, polyester, rubber and rubber-acrylic hybrid with a weight average molecular weight (Mw) of 5,000 to 1,000,000, and the layer has a thickness is from 0.2 to 3 mil (0.00508 to 0.0762 mm).

13. The multilayer time indicator kit of claim 3 in which the polymer resin of the timing layer is at least one of polyurethane, polyester, acrylic, polyvinyl chloride the pigment of the timing layer is aluminum flake and/or titanium dioxide (TiO$_2$), and the layer has a thickness from 0.2 to 3 mil (0.00508 to 0.0762 mm).

14. The multilayer time indicator kit of claim 3 in which the polymer resin of the dye layer is at least one of polyurethane, polyester, acrylic, polyvinyl chloride, the dye of the dye layer is of the anthraquinone family, and the layer has a thickness from 0.001 to 1 mil (0.0000254 to 0.0254 mm).

15. The multilayer time indicator kit of claim 3 in which the substrate layer comprises a polymeric film or glassine paper.

16. The multilayer time indicator kit of claim 3 further including a pressure sensitive adhesive with an optional protective liner backing.

* * * * *